(12) United States Patent
Cupp et al.

(10) Patent No.: US 6,749,855 B2
(45) Date of Patent: Jun. 15, 2004

(54) METHODS OF USE OF RECOMBINANT VASOACTIVE PROTEIN FROM SALIVARY GLAND OF THE BLACK FLY

(75) Inventors: Mary S. Cupp, Auburn, AL (US); Jose M. C. Ribeiro, Rockville, MD (US); Eddie W. Cupp, Auburn, AL (US)

(73) Assignees: Auburn University, Auburn, AL (US); University of Arizona, Tuscon, AZ (US)

( * ) Notice: Subject to any disclaimer, the term of this patent is extended or adjusted under 35 U.S.C. 154(b) by 0 days.

(21) Appl. No.: 10/218,699

(22) Filed: Aug. 14, 2002

(65) Prior Publication Data

US 2003/0012795 A1 Jan. 16, 2003

Related U.S. Application Data

(62) Division of application No. 09/702,647, filed on Oct. 31, 2000, now Pat. No. 6,500,420, which is a division of application No. 09/036,355, filed on Mar. 6, 1998, now Pat. No. 6,162,785.
(60) Provisional application No. 60/040,418, filed on Mar. 13, 1997.

(51) Int. Cl.[7] ............................................. A61K 39/015
(52) U.S. Cl. ....................................... 424/185.1; 514/12
(58) Field of Search .......................... 424/185.1; 514/12

(56) References Cited

U.S. PATENT DOCUMENTS

| 5,397,772 A | 3/1995 | Ribeiro et al. |
| 5,480,864 A | 1/1996 | Tajima et al. |
| 5,646,115 A | 7/1997 | Frank et al. |

FOREIGN PATENT DOCUMENTS

| WO | US98/04795 | 3/1998 |

OTHER PUBLICATIONS

Tilton et al, J of International Cardiology 12(2): 117–132; 1999, Abstract.*
Talley et al, Expert opinion on Investigational Drugs 10(7): 1291–308; 2001.*
Ribeiro (1992) "Characterization of a Vasodilator from the Salivary Glands of the Yellow Fever Mosquito *Aedes Aegypti*" *J. Exp. Biol.* 165:61–71.
Ribeiro et al. (1993) "The Salivary Catechol Oxidase/Peroxidase Activities of the Mosquito *Anopheles Albimanus*" *J. Exp. Biol.* 179:273–287.
Cross et al. (1994) "Differential Modulation of Murine Cellular Immune Responses by Salivary Gland Extract of *Aedes Aegypti*" *Am. J. Trop. Med. Hyg.* 51(5):690–696.
Cupp et al. (1994) "Vasodilative Activity in Black Fly Salivary Glands" *Am. J. Trop. Med. Hyg.* 50(2):241–246.
Qureshi et al. (1996) "Immunomodulatory Properties of Maxadilan, the Vasodilator Peptide from Sand Fly Salivary Gland Extracts" *Am. J. Trop. Med. Hyg.* 54(6):665–671.
Cupp et al., "Analysis of Black Fly Saliva and Its Relationship to Vector Status," Abstract of oral presentation to the XY International Congress of Entomology, Sep. 1996, Firenze, Italiae.

* cited by examiner

*Primary Examiner*—Christina Chan
*Assistant Examiner*—Phuong Huynh
(74) *Attorney, Agent, or Firm*—Alston & Bird LLP

(57) ABSTRACT

The invention is drawn to vasodilative proteins from the salivary glands of the species, Simulium. The protein additionally has immunomodulating activities. Methods for recombinant production of the protein as well as biomedical uses are provided.

5 Claims, 1 Drawing Sheet

Presence of erythema in NZW rabbit following intradermal injection of
SGE of female *S. vittatum* or rSVEP

| Protein source | quantity/reactivity | | | | | | | |
|---|---|---|---|---|---|---|---|---|
| SGE (pairs of glands) | 1 | 0.5 | 0.05 | 0.03 | 0.025 | 0.020 | 0.017 | 0.014 |
|  | + | + | + | + | + | + | + | - |
| r SVEP (ng) | 1,650 | 165 | 82.5 | 8.25 | 4.125 | 2.06 | 1.03 | 0.51 |
|  | + | + | + | + | + | + | + | - |

FIGURE 1

METHODS OF USE OF RECOMBINANT VASOACTIVE PROTEIN FROM SALIVARY GLAND OF THE BLACK FLY

CROSS-REFERENCE TO RELATED APPLICATIONS

This application is a divisional application of U.S. patent application Ser. No. 09/702,647, filed Oct. 31, 2000, now issued as U.S. Pat. No. 6,500,420, which is a divisional application of U.S. patent application Ser. No. 09/036,355 filed Mar. 6, 1998, now issued as U.S. Pat. No. 6,162,785, which claims the benefit of U.S. Provisional Application No. 60/040,418, filed Mar. 13, 1997.

FIELD OF THE INVENTION

The invention relates to the production of recombinant proteins and their use in biomedical therapies.

BACKGROUND OF THE INVENTION

Hypertension is the most common cardiovascular disease. Many people in the United States suffer from what is commonly referred to as "high blood pressure." That is, have a systolic and/or diastolic blood pressure above 140/90.

Elevated arterial pressure causes pathological changes in the vasculatury and hypertrophy of the left ventricle. As a consequence, hypertension has many deleterious effects on the body. For example, it is the principal cause of stroke, leads to disease of the coronary arteries with myocardial infarction and sudden cardiac death, and is a major contributor to cardiac failure, renal insufficiency, and dissecting aneurism of the aorta.

Pharmacological treatment of patients with high blood pressure will reduce morbidity, disability, and mortality from cardiovascular disease. Effective antihypertensive therapy will almost completely prevent hemorrhagic strokes, cardiac failure, and renal insufficiency due to hypertension. Overall, there is a marked reduction in total strokes.

Antihypertensive drugs can be classified according to their sites or mechanisms of action. Arterial pressure is the product of cardiac output and peripheral vascular resistance. Thus, such pressure can be lowered by actions of drugs on either the peripheral resistance or the cardiac output, or both. Drugs may reduce the cardiac output by either inhibiting myocardial contractility or decreasing ventricular filling pressure. Reduction in ventricular filling pressure may be achieved by actions on the venous tone or on blood volume via renal effects. Drugs can reduce peripheral resistance by acting on smooth muscle to cause relaxation of resistance vessels or by interfering with the activity of systems that produce constriction of resistance vessels.

Vasodilators are a class of drugs which are commonly employed in the therapy of heart failure, high blood pressure, and other various conditions characterized by constricted blood vessels. Such conditions include Raynaud's syndrome, certain post-surgical complications of brain surgery involving subarachnoid hemorrhage, heart failure, angina pectoris, and hypertension.

Proteins from biting insects, particularly blood-feeding arthropods, have been shown to contain numerous pharmacologically-active substances, including vasodilating substances. The saliva from such insects contain such substances to counteract many of the host's hemostatic defenses. Among these secretions are the potent vasodilating substances that heighten blood flow to the feeding site.

The salivary components responsible for vasodilation are extremely varied as revealed by the recent characterization of purified factors from several genera. Of several species of ticks analyzed, the saliva of each contained a lipid-derived prostaglandin that could account for vasodilative activity. Further, vasodilators play a role in skin-associated immune response.

Specific immunity has evolved as a sophisticated defense mechanism of higher organisms. In humans, cell-mediated immunity and humoral immunity are the two major mechanisms. Both of these responses have a high level of specificity directed to antigenic epitopes expressed on molecular components of foreign agents.

There are several clinical settings where it is desirable to suppress an immune response. These situations include organ transplantation, treatment of autoimmune disorders, and prevention of Rh hemolytic disease of the newborn.

Because of the importance of providing hypertension therapies, potent vasodilators are needed. Additionally, agents which are capable of modulating the immune response and aiding in wound healing are additionally desirable.

SUMMARY OF THE INVENTION

Purified vasoactive proteins from the salivary glands of the blood-feeding black fly, Simulium sp. are provided. The proteins find use in biomedical therapies, particularly where peripheral resistance and stenoses are problems. The proteins are also useful as regulators of the immune response and as promoters of wound healing.

The nucleotide sequence encoding the proteins, as well as methods for producing recombinant protein, are additionally provided.

BRIEF DESCRIPTION OF THE DRAWINGS

FIG. 1 shows the presence of erythema in NZW rabbits following intradermal injection of SGE of female S. vittatum or rSVEP.

DETAILED DESCRIPTION OF THE INVENTION

Methods and compositions for use as therapeutic vasodilating agents, i.e., as regulators of blood pressure are provided. The agents can be used to regulate blood flow to a wound site promoting wound healing. Additionally, the compositions of the invention can be utilized to modulate the immune response.

The compositions of the invention comprise vasoactive proteins from the salivary glands of the blood-feeding black fly. The proteins exhibit vasodilative activity and wound healing promoting properties, as well as the capacity to suppress certain immune responses in a mammal. Substantially purified preparations of the proteins are provided. Such substantially purified preparations include protein substantially free of any compound normally associated with the protein in its natural state. Such proteins can be assessed for purity by SDS-PAGE, chromatography, electrophoresis or other methods known in the art. See, M. P. Deutscher (ed.), *Guide to Protein Purification, Academic Press, Inc.* (1990).

The terms substantially pure or substantially purified are not meant to exclude artificial or synthetic mixtures of the protein with other compounds. It is recognized that the vasoactive proteins of the present invention include those proteins homologous to, and having essentially the same biological properties as, the vasoactive protein described herein, and particularly the protein disclosed herein in SEQ ID NO: 2. This definition is intended to encompass natural allelic variations in the genes.

The invention additionally encompasses the nucleotide sequences, which encode the proteins of the invention. The nucleotide sequence of the coding sequence from *S. vittatum* is provided in SEQ ID NO: 1. Additionally, cloned genes of the present invention can be of other species of origin. Thus, DNAs which hybridize to the nucleotide sequence of the vasoactive gene from the black fly are also an aspect of this invention. Conditions, which will permit other DNAs to hybridize to the DNA disclosed herein, can be determined in accordance with known techniques. For example, hybridization of such sequences may be carried out under conditions of reduced stringency, medium stringency or even stringent conditions (e.g., conditions represented by a wash stringency of 35–40% Formamide with 5× Denhardt's solution, 0.5% SDS and 1× SSPE at 37° C.; conditions represented by a wash stringency of 40–45% Formamide with 5× Denhardt's solution, 0.5% SDS, and 1× SSPE at 42° C.; and conditions represented by a wash stringency of 50% Formamide with 5× Denhardt's solution, 0.5% SS and 1× SSPE at 42° C., respectively, to DNA encoding the vasoactive genes disclosed herein in a standard hybridization assay. See J. Sambrook et al., Molecular Cloning, A Laboratory Manual (2d Ed. 1989) (Cold Spring Harbor Laboratory).

In general, sequences which code for the vasoactive protein and hybridize to the nucleotide sequence disclosed herein will be at least 75% homologous, 85% homologous, and even 95% homologous or more with the sequences. Further, the amino acid sequences of the vasoactive proteins isolated by hybridization to the DNA's disclosed herein are also an aspect of this invention. The degeneracy of the genetic code, which allows different nucleic acid sequences to code for the same protein or peptide, is well known in the literature. See, e.g., U.S. Pat. No. 4,757,006.

The hybridization probes may be cDNA fragments or oligonucleotides, and may be labeled with a detectable group as known in the art. Pairs of probes which will serve as PCR primers for the vasoactive gene or a protein thereof may be used in accordance with the process described in U.S. Pat. Nos. 4,683,202 and 4,683,195.

It is recognized that the nucleotide and peptide sequences of the invention may be altered in various ways including amino acid substitutions, deletions, truncations, and insertions. Methods for such manipulations are generally known in the art. For example, amino acid sequence variants of the peptides and proteins can be prepared by mutations in the DNA. Methods for mutagenesis and nucleotide sequence alterations are well known in the art. See, for example, Kunkel, T. (1985) *Proc. Natl. Acad. Sci. USA* 82:488–492; Kunkel et al. (1987) *Methods in Enzymol.* 154:367–382; U.S. Pat. No. 4,873,192; Walker and Gaastra (eds.) *Techniques in Molecular Biology*, MacMillan Publishing Company, N.Y. (1983) and the references cited therein. Thus, the nucleotide sequences of the invention include both the naturally occurring sequences as well as mutant forms. Likewise, the peptides and proteins of the invention encompass both naturally occurring and modified forms thereof. Such variants will continue to possess the desired activity. Obviously, the mutations that will be made in the DNA encoding the variant must not place the sequence out of reading frame and preferably will not create sequences deleterious to expression of the gene product. See, EP Patent Application Publication No. 75,444.

Thus proteins of the invention include the naturally occurring forms as well as variants thereof. These variants will be substantially homologous and functionally equivalent to the native protein. A variant of a native protein is "substantially homologous" to the native protein when at least about 80%, more preferably at least about 90%, and most preferably at least about 95% of its amino acid sequence is identical to the amino acid sequence of the native protein. A variant may differ by as few as 1, 2, 3, or 4 amino acids. By "functionally equivalent" is intended that the sequence of the variant defines a chain that produces a protein having substantially the same biological activity as the native protein of interest. Such functionally equivalent variants that comprise substantial sequence variations are also encompassed by the invention. Thus a functionally equivalent variant of the native protein will have a sufficient biological activity to be therapeutically useful. By "therapeutically useful" is intended effective in achieving a therapeutic goal as discussed in more detail below.

Methods are available in the art for determining functional equivalence. Biological activity can be measured using assays specifically designed for measuring activity of the native protein, including assays described in the present invention. Additionally, antibodies raised against the biologically active native protein can be tested for their ability to bind to the functionally equivalent variant, where effective binding is indicative of a protein having conformation similar to that of the native protein.

DNA sequences can also be synthesized chemically or modified by site-directed mutagenesis to reflect the codon preference of the host cell and increase the expression efficiency.

The proteins of the invention can be "engineered" in accordance with the present invention by chemical methods or molecular biology techniques. Molecular biology methods are most convenient since proteins can be engineered by manipulating the DNA sequences encoding them. Genomic DNA, cDNA, synthetic DNA, and any combination thereof may be used for this purpose. Genomic DNA sequences or cDNA sequences encoding proteins can be isolated based on the amino acid sequence of proteins or certain protein properties. Many methods of sequence isolation are known in the art of molecular biology. See particularly Sambrook et al. (1989) *Molecular Cloning: A Laboratory Manual* (Cold Spring Harbor Laboratory Press, Plainview, N.Y.), herein incorporated by reference.

Once the nucleotide sequences encoding the vasoactive proteins of the invention have been isolated, they can be manipulated and used to express the protein in a variety of hosts including other organisms, including microorganisms.

Once the nucleotide sequence is identified and known, those skilled in the art can produce large quantities of the protein for therapeutic use. Accordingly, recombinant protein and methods for producing the recombinant protein are encompassed by the present invention. In this manner, the nucleotide sequence encoding the vasoactive protein can be utilized in vectors for expression in various types of host cells, including both procaryotes and eucaryotes, to produce large quantities of the protein, or active analogues, or fragments thereof, and other constructs capable of inducing vasodilation or temporarily suppress the immune response in a mammal.

Generally, methods for the expression of recombinant DNA are known in the art. See, for example, Sambrook et al. *Molecular Cloning*, Cold Spring Harbor Laboratory (1989). Additionally, host cells and expression vectors, such as the baculovirus expression vector may be employed in carrying out the present invention, as described in U.S. Pat.

Nos. 4,745,051 and 4,879,236. In general, a baculovirus expression vector comprises a baculovirus genome containing the gene to be expressed inserted into the polyhedron gene at a position ranging from the polyhedron transcriptional start signal to the ATG start site and under the transcriptional control of a baculovirus polyhedron promoter.

A broad variety of suitable procaryotic and microbial vectors are available. Likewise, the promoters and other regulatory agents used in expression of foreign proteins are available in the art. Promoters commonly used in recombinant microbial expression vectors are known in the art and include the beta-lictamase (penicillinase) and lactose promoter systems (Chang et al. (1978) *Nature,* 275:615 and Goeddel et al. (1979) *Nature,* 281:544); A tryptophan (TRP) promoter system (Goeddel et al. (1980) *Nucleic Acids Res.,* 8:4057 and the EPO Application Publication No. 36,776); and the Tac promoter (DeBoer et al. (1983) *Proc. Natl. Acad. Sci. USA,* 80:21). While these are commonly used, other microbial promoters are available. Details concerning nucleotide sequences of many have been published, enabling a skilled worker to operably ligate them to DNA encoding the protein in plasmid or viral vectors. See, for example, Siedenlist et al. (1980) *Cell* 20:269.

Eukaryotic microbes such as yeast may be transformed with suitable protein-encoding vectors. See, e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the desired protein, sequences for polyadenylation and transcription termination, and a selection gene. An exemplary plasmid is YRp7, (Stinchcomb et al. (1979) *Nature,* 282:9; Kingsman et al. (1979) *Gene,* 7:141; Tschemper et al. (1980) *Gene,* 10:157). This plasmid contains the trp 1 gene, which provides a selection marker for a mutant strain of yeast lacking the ability to grow in tryptophan, for example ATCC No. 44076 or PEP4-1 (Jones, *Genetics* 85, 12 (1977)). The presence of the trp 1 lesion in the yeast host cell genome then provides an effective environment for detecting transformation by growth in the absence of tryptophan.

Suitable promoting sequences in yeast vectors include the promoters for metallothionein, alcohol dehydrogenase, adenylate cyclase, 3-phosphoglycerate kinase (Hitzeman et al. (1980) *J. Biol. Chem.* 255:2073) and other glycolytic enzymes (Hess et al. (1968) *J. Adv. Enzyme Reg.,* 7:149; and Holland et al. (1978) *Biochemistry,* 17:4900) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al. EPO Publication. No. 73,657.

The compositions of the present invention can be formulated into pharmaceutical preparations for therapeutic use. As a vasodilator, the compositions find use for atherosclerosis of extremities, for heart failure, for hypertension, for peripheral resistance, stenoses, and the like, particularly peripheral vasodilation.

The compositions of the invention can also be used to temporarily suppress the immune system. In this manner, a mammal can be desensitized to the effects of an immunogen by parenteral administration of the vasoactive protein, active analogs or fragments thereof. For modulating the immune system, the proteins can be utilized to inhibit or prevent the development of antibodies or cellular immunity to a protein, to treat graft rejection, autoimmune diseases, and the like.

The compositions of the invention find use as promoters of wound healing. Application to the wound site results in an increased rate of healing.

The compositions of the invention can be used alone or in combination with other vasoactive and therapeutic agents. Other agents are known in the art.

The vasoactive compositions can be formulated according to known methods to prepare pharmaceutically useful compositions, such as by admixture with a pharmaceutically acceptable carrier vehicle. Suitable vehicles and their formulation are described, for example, in *Remington's Pharmaceutical Sciences* 16th ed., Osol, A. (ed.), Mack Easton Pa. (1980). In order to form a pharmaceutically acceptable composition suitable for effective administration, such compositions will contain an effective amount of the vasoactive protein, either alone, or with a suitable amount of carrier vehicle.

Additional pharmaceutical methods may be employed to control the duration of action. Controlled release preparations may be achieved by the use of polymers to complex or absorb the antiviral compositions. The controlled delivery may be exercised by selecting appropriate macro molecules (for example, polyesters, polyamino acids, polyvinyl pyrrolidone, ethylene-vinylacetate, methylcellulose, carbosymethylcellulose, or protamine sulfate). The rate of drug release may also be controlled by altering the concentration of such macromolecules.

Another possible method for controlling the duration of action comprises incorporating the therapeutic agents into particles of a polymeric substance such as polyesters, polyamiono acids, hydrogels, poly(lactic acid) or ethylene vinylacetate copolymers. Alternatively, it is possible to entrap the therapeutic agents in microcapsules prepared, for example, by coacervation techniques or by interfacial polymerization, for example, by the use of hydroxymethyl cellulose or gelatin-microcapsules or poly(methylmethacrylate) microcapsules, respectively, or in a colloid drug delivery system, for example, liposomes, albumin, microspheres, microemulsions, nanoparticles, nanocapsules, or in macroemulsions. Such teachings are disclosed in *Remington's Pharmaceutical Sciences* (1980).

It is contemplated that the inhibitory compositions of the present invention will be administered by an individual in therapeutically effective amounts. That is, in an amount sufficient to regulate blood pressure and/or suppress the immune response. The effective amount of the composition will vary according to the weight, sex, age, and medical history of the individual. Other factors which influence the effective amount may include, but are not limited to, the severity of the patient's condition, the stability of the vasoactive protein, the kinetics of interaction in the recipient, previous exposure to the vasoactive protein, kidney or other disease, etc. Typically, for a human subject, an effective amount will range from about 0.1 ng to about 100 mg, specifically, from about 1 ng to about 10 mg, more specifically from about 10 ng to about 1 mg.

The pharmaceutically prepared inhibitory compositions of the invention may be provided to a patient by means will known in the art. Such means of introduction include oral means, intranasal means, subcutaneous means, intramuscular means, topical, intradermal means, intravenous means, intraarterial means, or parenteral means.

The vasoactive proteins of the present invention may be dissolved in any physiologically tolerated liquid in order to prepare an injectable bolus. It is generally preferable to prepare such a bolus by dissolving the molecule in normal saline.

The following examples are offered by way of illustration and not by way of limitation.

EXPERIMENTAL

Many modifications and other embodiments of the invention will come to mind in one skilled in the art to which this invention pertains having the benefit of the teachings presented in the foregoing descriptions and the associated drawings. Therefore, it is to be understood that the invention is not to be limited to the specific embodiments disclosed. Although specific terms are employed, they are used in a generic and descriptive sense only and not for purposes of limitation, and that modifications and embodiments are intended to be included within the scope of the appended claims.

Salivary gland extracts of several Simulium were shown to contain vasodilative activity as measured by the rapid and persistent induction of erythema in response to intradermal injection into rabbit skin. Tests for physical stability of the activities indicated that the vasodilators were proteinaceous and heat stable. The electrospray ionization mass spectroscopy of the *S. vittatum* protein detected a mass of about 15,000 Daltons.

Methods for the construction of *S. vittatum* salivary gland cDNA library and cloning of specific cDNA of *Simulium vittatum* salivary gland erythema protein (SVEP) was performed by the following steps:

1. SVEP was purified from salivary glands and sent to the Harvard Microchemistry Laboratory where it was subjected to limited digestion with trypsin. Two peptides, CT29 (SEQ ID NO: 3) and CT51 (SEQ ID NO: 4) were sequenced by an automated Edman degradation procedure.
2. Messenger RNA (mRNA) was isolated from SGE of *S. vittatum*. A commercially-available kit was used to prepare the cDNA library (ZAP EXPRESS™ cDNA synthesis kit, Strategene, La Jolla, Calif.).
3. A fragment of the SVEP cDNA was generated by PCR using degenerate primers that were designed based on knowledge of the partial amino acid sequence revealed in sequencing of the purified protein. A commercially available kit (TA Cloning® System, Invitrogen) was used to clone the PCR product. Sequencing of the cDNA and comparison of the translated amino acid sequence confirmed the validity of the clone. Further, the relative order of the two peptides and the intervening amino acids were determined (SEQ ID NO: 5). A digoxigenin-labeled (DIG) probe was generated for use in screening the cDNA library to recover the full-length clone.
4. Screening of the library produced a full-length clone that provided the remaining codes for all the amino acids, including a hydrophobic leader sequence that is cleaved from the mature, functional protein. Analysis of the remaining bases revealed that the mRNA for this protein has a relative small number of non-translated base sequences at the N and C termini (SEQ ID NO: 1).
5. Calculation of the putative molecular weight of the mature protein which would be generated by the cDNA clone was 15,348.9 Daltons, which is 1.23 to 2.58 Daltons less than the weight of the HPLC purified protein determined by ESIMS.

C. Production of Recombinant SVEP Protein (rSVEP) Via Baculovirus Expression System 1. A commercially available baculovirus vector (pBacPAK8, Clontech Laboratories, Inc., Palo Alto, Calif.) and cDNA of SVEP were digested with PstI and XhoI restriction enzymes and religated to form a recombinant plasmid.
2. Recombinant virus was produced by co-infection of Sf9 cells with the pBacPAK8/SVEP and baculovirus DNA digested with BSU36I.
3. Recombinant virus was purified by plaque assay and amplified.
4. Production of SVEP DNA in the recombinant virus was confirmed by PCR amplification of cellular DNA isolated from infected cultures.
5. Synthesis and secretion of protein of the appropriate molecular weight was demonstrated in SDS/PAGE of proteins present in the cellular cultures of recombinant-virus infected cells and absent from cellular supernatants of wild-type virus infected cells.

D. Quantitative Analysis of rSVEP

1. By examination of silver-stained, SDS protein gels, it was determined that rSVEP was ≧90% of the total protein in cell culture supernatants at 48 hr post infection.
2. Total protein concentration was determined using the Lowry method. Based on the observations of #1 above, rSVEP protein concentration was estimated as the difference between total protein concentration in cellular supernatants of BV/SVEP infected cells and wild-type infected cells.
3. Using these quantitative measurements, the potency of rSVEP was estimated by bioassay in rabbit skin as described previously. The limit of detectable erythema following injection was approximately 1 ng, and was equivalent to the activity present in 0.017 pairs of *S. vittatum* salivary glands. For a protein of molecular weight 15,315 Daltons, this is equivalent to 65 femtomoles (FIG. 1).

E. Physical Properties of rSVEP

1. Native and recombinant SVEP have a compact tertiary structure that causes the protein to migrate at a faster rate, when subjected to gel sieving techniques, than would be predicted by molecular weight alone. Treatment with the disulfide reducing reagent, 2-mercaptoethanol, delays mobility and thus indicates that the two cysteines form a disulfide bond. Because these two amino acids are located at the two different ends of the sequence, substantial folding of the protein must occur to accommodate bond formation.
2. Amino acid composition of SVEP shows a relative high percentage of basic amino acids (see SEQ ID NO: 2; lysine, coded as K, and arginine, coded as R). Based on TSK gel sieving and protein staining patterns it is likely that the folded protein displays these basic moieties on its surface to produce a positively charged molecule.

F. Therapeutic Uses of rSVEP

1. Test of rSVEP efficacy in facilitating wound healing.
   a. Using NZW rabbits, sterile, surgical open and closed wounds will be created. rSVEP or control solution will be injected intradermally or subcutaneously on a daily basis.
   b. Differentiation of vasoactive effects from inflammation will be determined using 1) laser doppler imagery for reperfusion, 2) histopathological evaluation for granulation tissue and 3) measurement of inflammatory cytokines, I11α, I11β and TNFα.

c. The rate of healing will be determined using 3 measures: Planimetry to determine rate of open wound healing, histological evaluation to determine progression from inflammatory stage to repair stage, and tensiometry to determine strength of tissue repair.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed is:

1. A method for lowering peripheral vascular resistance in a mammal, said method comprising administering a therapeutically effective amount of a polypeptide comprising the amino acid sequence set forth in SEQ ID NO: 2, that increases blood flow whereby the peripheral vascular resistance is lowered.

2. A method for lowering peripheral vascular resistance in a mammal, said method comprising administering a therapeutically effective amount of a polypeptide comprising the mature form of the amino acid sequence of SEQ ID NO:2 that increases blood flow, whereby the peripheral vascular resistance is lowered.

3. The method of claim 1, wherein said polypeptide is produced by recombinant methods.

4. A method for lowering peripheral vascular resistance in a mammal, said method comprising administering a therapeutically effective amount of a polypeptide encoded by a nucleotide sequence comprising the sequence set forth in nucleotides 49 504 of SEQ ID NO:1 that increases blood flow, whereby the peripheral vascular resistance is lowered.

5. The method of claim 1, wherein said step of administering said polypeptide comprises administration by intradermal injection.

* * * * *

UNITED STATES PATENT AND TRADEMARK OFFICE
CERTIFICATE OF CORRECTION

PATENT NO. : 6,749,855 B2
DATED : June 15, 2004
INVENTOR(S) : Cupp et al.

It is certified that error appears in the above-identified patent and that said Letters Patent is hereby corrected as shown below:

Column 14,
Line 19, "49 504" should read -- 49-504 --.

Signed and Sealed this

Twenty-first Day of December, 2004

JON W. DUDAS
*Director of the United States Patent and Trademark Office*

SEQUENCE LISTING

```
<160> NUMBER OF SEQ ID NOS: 5

<210> SEQ ID NO 1
<211> LENGTH: 548
<212> TYPE: DNA
<213> ORGANISM: Simulium vittatum
<220> FEATURE:
<221> NAME/KEY: CDS
<222> LOCATION: (49)...(507)

<400> SEQUENCE: 1
ctgaagtgta aagtacttaa atcattcggt gggaattatc cagcaagt atg agc atc      57
                                                    Met Ser Ile
                                                     1 aca caa agc ttc ttt gtt tta acc ctt gcc ata ttt ggt gct gca tca     105
Thr Gln Ser Phe Phe Val Leu Thr Leu Ala Ile Phe Gly Ala Ala Ser
     5                  10                  15 gac aac cca att gct gat aga aaa tgt atc gtc atc agt gac ggg gac     153
Asp Asn Pro Ile Ala Asp Arg Lys Cys Ile Val Ile Ser Asp Gly Asp
 20                  25                  30                  35 ctg gtt atg cac gag cga aaa ccc ggt caa gag ttc cca tac tat gtc     201
Leu Val Met His Glu Arg Lys Pro Gly Gln Glu Phe Pro Tyr Tyr Val
                 40                  45                  50 tac atg atc ccg aag ggt aca gag tac gac gat caa cga tgg atc ctg     249
Tyr Met Ile Pro Lys Gly Thr Glu Tyr Asp Asp Gln Arg Trp Ile Leu
             55                  60                  65 gag agt gtg gga gga gat cac tat aag ctg aag aac aag ttt tcc gga     297
Glu Ser Val Gly Gly Asp His Tyr Lys Leu Lys Asn Lys Phe Ser Gly
         70                  75                  80 cgg tat ttg gtg tat ggc acc ttt gat tat ttc ctc acg gca gga gca     345
Arg Tyr Leu Val Tyr Gly Thr Phe Asp Tyr Phe Leu Thr Ala Gly Ala
     85                  90                  95 gcc gtc aga gag atg gat cat ttc aaa ttc act gct gat ggg acg ggc     393
Ala Val Arg Glu Met Asp His Phe Lys Phe Thr Ala Asp Gly Thr Gly
100                 105                 110                 115 aag tat gac atc tct agc aaa gcg aat ggt cat cct cga tct cgc ggc     441
Lys Tyr Asp Ile Ser Ser Lys Ala Asn Gly His Pro Arg Ser Arg Gly
                120                 125                 130 aaa aat tgg gga gtc atg aaa gat ggt gag aag cac tat ttc act gtt     489
Lys Asn Trp Gly Val Met Lys Asp Gly Glu Lys His Tyr Phe Thr Val
            135                 140                 145 gaa aat tgt cag gaa taa taaataagaa atgttgaagt tgaaaaaaaa            537
Glu Asn Cys Gln Glu *
            150 aaaaaaaaaa a                                                        548

<210> SEQ ID NO 2
<211> LENGTH: 152
```

-continued

<212> TYPE: PRT
<213> ORGANISM: Simulium vittatum

<400> SEQUENCE: 2

Met Ser Ile Thr Gln Ser Phe Phe Val Leu Thr Leu Ala Ile Phe Gly
1 5 10 15

Ala Ala Ser Asp Asn Pro Ile Ala Asp Arg Lys Cys Ile Val Ile Ser
20 25 30

Asp Gly Asp Leu Val Met His Glu Arg Lys Pro Gly Gln Glu Phe Pro
35 40 45

Tyr Tyr Val Tyr Met Ile Pro Lys Gly Thr Glu Tyr Asp Asp Gln Arg
50 55 60

Trp Ile Leu Glu Ser Val Gly Gly Asp His Tyr Lys Leu Lys Asn Lys
65 70 75 80

Phe Ser Gly Arg Tyr Leu Val Tyr Gly Thr Phe Asp Tyr Phe Leu Thr
85 90 95

Ala Gly Ala Ala Val Arg Glu Met Asp His Phe Lys Phe Thr Ala Asp
100 105 110

Gly Thr Gly Lys Tyr Asp Ile Ser Ser Lys Ala Asn Gly His Pro Arg
115 120 125

Ser Arg Gly Lys Asn Trp Gly Val Met Lys Asp Gly Glu Lys His Tyr
130 135 140

Phe Thr Val Glu Asn Cys Gln Glu
145 150

<210> SEQ ID NO 3
<211> LENGTH: 22
<212> TYPE: PRT
<213> ORGANISM: Simulium vittatum

<400> SEQUENCE: 3

Gly Lys Asn Trp Gly Val Met Lys Asp Gly Glu Lys His Tyr Phe Thr
1 5 10 15

Val Glu Asn Cys Gln Glu
20

<210> SEQ ID NO 4
<211> LENGTH: 15
<212> TYPE: PRT
<213> ORGANISM: Simulium vittatum

<400> SEQUENCE: 4

Lys Pro Gly Gln Glu Phe Pro Tyr Tyr Val Tyr Met Ile Pro Lys
1 5 10 15

<210> SEQ ID NO 5
<211> LENGTH: 109
<212> TYPE: PRT
<213> ORGANISM: Simulium vittatum

<400> SEQUENCE: 5

Lys Pro Gly Gln Glu Phe Pro Tyr Tyr Val Tyr Met Ile Pro Lys Gly
1 5 10 15

Thr Glu Tyr Asp Asp Gln Arg Trp Ile Leu Glu Ser Val Gly Gly Asp
20 25 30

His Tyr Lys Leu Lys Asn Lys Phe Ser Gly Arg Tyr Leu Val Tyr Gly
35 40 45

Thr Phe Asp Tyr Phe Leu Thr Ala Gly Ala Ala Val Arg Glu Met Asp
50 55 60

```
-continued

His Phe Lys Phe Thr Ala Asp Gly Thr Gly Lys Tyr Asp Ile Ser Ser
 65                  70                  75                  80

Lys Ala Asn Gly His Pro Arg Ser Arg Gly Lys Asn Trp Gly Val Met
                 85                  90                  95

Lys Asp Gly Glu Lys His Tyr Phe Thr Val Glu Asn Cys
            100             105
```